(12) United States Patent
Shi et al.

(10) Patent No.: US 11,853,019 B1
(45) Date of Patent: Dec. 26, 2023

(54) INTELLIGENT CONTROL OF SPUNLACE PRODUCTION LINE USING CLASSIFICATION OF CURRENT PRODUCTION STATE OF REAL-TIME PRODUCTION LINE DATA

(71) Applicant: Jinan Winson New Materials Technology Co., Ltd., Jinan (CN)

(72) Inventors: Xiaohui Shi, Jinan (CN); Zhenwu Ma, Jinan (CN); Tengfei Ma, Jinan (CN); Shizhao Peng, Jinan (CN); Ke Shi, Jinan (CN); Dongpeng Song, Jinan (CN); Yijun Liu, Jinan (CN); Wei Wang, Jinan (CN)

(73) Assignee: Jinan Winson New Materials Technology Co., Ltd., Jinan (CN)

( * ) Notice: Subject to any disclaimer, the term of this patent is extended or adjusted under 35 U.S.C. 154(b) by 0 days.

(21) Appl. No.: 18/145,696

(22) Filed: Dec. 22, 2022

(30) Foreign Application Priority Data

Aug. 31, 2022 (CN) .......................... 202211063196.X

(51) Int. Cl.
*G05B 13/04* (2006.01)
*A61F 13/15* (2006.01)
(Continued)

(52) U.S. Cl.
CPC ......... *G05B 13/042* (2013.01); *G05B 13/048* (2013.01); *A61F 2013/15821* (2013.01);
(Continued)

(58) Field of Classification Search
CPC .. G05B 13/042; G05B 13/048; G05B 19/418; G05B 2219/21002; A61F 2013/15821; A61F 2013/15983; B32B 5/067
See application file for complete search history.

(56) References Cited

U.S. PATENT DOCUMENTS

| | | | |
|---|---|---|---|
| 2006/0079143 A1* | 4/2006 | Phan | A61L 2/26 427/289 |
| 2020/0166909 A1* | 5/2020 | Noone | G06N 20/00 |

(Continued)

FOREIGN PATENT DOCUMENTS

| | | |
|---|---|---|
| CN | 109947088 A | 6/2019 |
| CN | 110390348 A | 10/2019 |

(Continued)

OTHER PUBLICATIONS

Amit Kumar Gope, "Quality Prediction and Abnormal Processing Parameter Identification in Polypropylene Fiber Melt Spinning Using AI ML and Deep Learning Algorithms", Jul. 4, 2022, Polymers, 14, 2739. URL :<https://www.ncbi.nlm.nih.gov/pmc/articles/PMC9269265/pdf/polymers (Year: 2022).*

(Continued)

*Primary Examiner* — Kenneth M Lo
*Assistant Examiner* — Jonathan Michael Skrzycki
(74) *Attorney, Agent, or Firm* — Rachel Pilloff; Sean Passino; Martin Cosenza

(57) ABSTRACT

Disclosed is an intelligent control system of spunlace production line, which includes a data acquiring module, which is used for acquiring and storing real-time production line data; the production line data includes cotton feeding roller value, real-time moisture value, real-time speed value and real-time gram weight value; the data process module is used for classify and controlling that production line data, and giving the adjustment opinions of the cotton feeding roller parameters; the parameter control module is used for verifying the parameter adjustment opinions and applying the opinions to the control system; the data acquiring module, the data processing module and the parameter control module are connected in sequence.

7 Claims, 13 Drawing Sheets

(51) Int. Cl.
*G05B 19/418* (2006.01)
*B32B 5/06* (2006.01)

(52) U.S. Cl.
CPC ..... *A61F 2013/15983* (2013.01); *B32B 5/067* (2021.05); *G05B 19/418* (2013.01); *G05B 2219/21002* (2013.01)

(56) References Cited

U.S. PATENT DOCUMENTS

| | | | |
|---|---|---|---|
| 2020/0285997 A1* | 9/2020 | Bhattacharyya | G06N 7/00 |
| 2020/0380336 A1 | 12/2020 | Chowdhury et al. | |
| 2021/0191363 A1* | 6/2021 | Mehr | B22F 10/28 |
| 2023/0081796 A1* | 3/2023 | Chourasia | H04R 25/75 |
| | | | 381/56 |

FOREIGN PATENT DOCUMENTS

| | | | | |
|---|---|---|---|---|
| CN | 110750640 A | | 2/2020 | |
| CN | 110782179 A | | 2/2020 | |
| CN | 110909977 A | | 3/2020 | |
| CN | 111338311 A | | 6/2020 | |
| CN | 111562496 A | | 8/2020 | |
| CN | 111914873 A | | 11/2020 | |
| CN | 113239998 A | | 8/2021 | |
| CN | 114282342 A | | 4/2022 | |
| CN | 114481077 A | | 5/2022 | |
| CN | 114528896 A | | 5/2022 | |
| CN | 114692950 A | | 7/2022 | |
| CN | 116224947 A | * | 6/2023 | |
| EP | 4079272 A1 | * | 10/2022 | |
| IN | 110991474 A | | 4/2020 | |
| WO | WO-2020228932 A1 | * | 11/2020 | ............. B25J 9/163 |

OTHER PUBLICATIONS

First Office Action issued in counterpart Chinese Patent Application No. 202211063196.X, dated Jan. 19, 2023.
Liu et al., Construction and application of big data intelligent interconnection platform for Xingcheng ironmaking, Metallurgical Industry Automation, vol. 45, No. 3, pp. 34-41, dated May 30, 2021.
Zhou, Intelligent manufacturing of spunlaced nonwovens, Automated application, Issue 02, 2020, pp. 144-145, dated Feb. 28, 2020.

* cited by examiner

INTELLIGENT CONTROL OF SPUNLACE PRODUCTION LINE USING CLASSIFICATION OF CURRENT PRODUCTION STATE OF REAL-TIME PRODUCTION LINE DATA

CROSS-REFERENCE TO RELATED APPLICATIONS

This application claims priority to Chinese Patent Application No. 202211063196.X, filed on Aug. 31, 2022, the contents of which are hereby incorporated by reference.

TECHNICAL FIELD

The application relates to the technical field of intelligent spunlace production, and in particular to an intelligent control system of a spunlace production line.

BACKGROUND

FIG. 1 shows some fragments of the process flow on the current spunlace production line. The spunlace production line has a high level of automation and informatization, and the relevant testing equipment on the production line continuously collect and analyze the quality index data. The workers on the production line may decide the parameter adjustment strategy of the production equipment in the relevant links according to analysis results.

The specific processes of "carding web" and "on-line monitoring", which have the highest correlation with the gram weight index, include: 1. carding web: the fiber temporary storage equipment stably transports fibers to the carding web equipment, and the fiber web is formed by the carding web equipment (air pressure cotton box, carding machine, cross lapping machine, multi-roller drafting machine, etc.). There are two sets of web laying equipment, each of which combs a layer of web, and then the upper and lower layers of web are combined and transported to the later spunlace process. The parameters of cotton feeding speed are controlled manually. When the cotton feeding speed is increased, the gram weight and thickness of the produced non-woven fabric will increase. 2. On-line monitoring: before the spunlaced cloth enters the winding equipment, there is a detection device (gram weight, moisture, thickness, defect detection). The scanner samples in one pass and displays it graphically based on the target value. Gram weight change is an index that represents frequent fluctuations. For example, the change of raw materials, uneven cotton feeding in front, the amount of moisture and so on may all lead to the change of gram weight.

At present, the operation of gram weight on the production line is mainly based on subjective judgment. When the curve exceeds the set threshold, the operator will adjust the cotton feeding amount on the console of the laying equipment. The adjustment of the gram weight will occur about a dozen to dozens of times every day.

Therefore, it can be seen that for the spunlaced production line, manual intervention is needed during the process of adjusting the equipment parameters according to the monitoring data. At present, most spunlaced nonwoven production lines in China adopt similar semi-automatic production according to the investigation.

Parameter adjustment with manual interference has the following defects:

The adjustment efficiency is not good with has time delay: the monitoring and adjustment of gram weight index account for most of the adjustment work in the production process. Moreover, because the distance between the monitoring online indicator equipment and the console for adjusting the weight of grams is far, it is not only laborious but also not timely for the master to reciprocate back and forth.

The adjustment is unstable. Master's adjustment of parameters is subjective, and there are no precise adjustment rules. The master increases or decreases the cotton feeding parameters by observing the curve obtained by online scanning. In order to solve the defect of manual interference in adjusting parameters, an intelligent control system of spunlace production line is urgently needed.

SUMMARY

The objective of the present application is to provide an intelligent control system of spunlace production line, so as to solve the defects of low efficiency and unstable adjustment of parameters by manual intervention in the prior art.

To achieve the above objective, the present application provides the following solutions.

An intelligent control system of a spunlace production line implemented in a computer system using a set of computer-executable instructions, including:

a data acquiring module used for acquiring and storing real-time production line data;

and the production line data includes cotton feeding roller values, real-time moisture values, real-time speed values and real-time gram weight values;

a data process module used for classifying and controlling the production line data, and giving adjustment opinions of cotton feeding roller parameters;

a parameter control module used for verifying parameter adjustment opinions and applying the parameter adjustment opinions to the intelligent control system; and the data acquiring module, the data processing module and the parameter control module are connected in sequence.

Optionally, the data acquiring module acquires the real-time production line data through sensors on the process production line, and saves the production line data into an influxDB (influxDataBase) time series database through KEPServer for subsequent modules to process and analyze.

Optionally, the data acquiring module further includes a preprocessing unit; the preprocessing unit is used for cleaning, segmenting and extracting the production line data, performing a data enhancement processing by adopting an up-sampling method or a down-sampling method to obtain preprocessed data, and storing the preprocessed data into the influxDB time series database.

Optionally, the data processing module includes:
a classifying unit used for predicting a probability of exceeding a gram weight threshold in the future through a classifying model; and
a control unit used for setting up an automatic control closed loop and giving the adjustment opinions of cotton feeding roller parameters.

Optionally, the classifying model is used for classification according to the real-time production line data to obtain current production states and classification results; defining label types for the classification results, and judging whether an adjustment operation is needed or not according to the classification results; if the adjustment operation is needed, the classification results are input into the control unit for a further processing, and if the adjustment operation is not needed, new data is continuously re-input.

Optionally, the classifying model adopts a double-layer classifier; the two-layer classifier includes a first classifier and a second classifier; taking an output quantity of the first classifier as an input quantity of the second classifier.

Optionally, the first classifier adopts a random forest model, performing a feature extraction of a historical gram weight window and a historical cotton feeding roller window, inputs the features into the random forest model, and outputs a predicted percentage of each label; the second classifier inputs a historical window of the predicted percentage of the output label of the first classifier by adopting a long short-term memory (LSTM), and outputs the predicted label of a production state; the LSTM model uses a small batch gradient descent method to train historical data, adjusts real-time data through random gradient descent, and obtains a probability of the label of the production state through a full connection layer activated by softmax.

Optionally, the control unit includes:
a prediction model used to predict the cotton feeding roller value output by the system in the future according to the historical production line data and the predicted percentage of labels;
an optimization sub-unit used for adjusting the cotton feeding roller value through the prediction model between a variable quantity of gram weight and the variable quantity of cotton feeding roller, using the prediction percentage of labels output by the classifying model as a membership degree of the classification of the production state, and outputting an optimal adjustment amount of the cotton feeding roller based on a model conversion.

Optionally, the parameter control module includes a feedback correction unit; the feedback correction unit is used for re-predicting at each new sampling moment, and correcting a prediction result using real-time information, and then performing a new optimization.

The application has the following beneficial effects.

According to the application, the relations between the change of gram weight and the change of cotton feeding roller parameters may be better established, the opinions of parameter adjustment may be output to workers in an intelligent way, and the automatic adjustment work may be completed; on the basis of ensuring the adjustment accuracy, a lot of manual work is saved, and an automatic closed loop of "monitoring, adjusting and changing" is completed through intelligent control.

BRIEF DESCRIPTION OF THE DRAWINGS

In order to more clearly explain the embodiments of the present application or the technical solutions in the prior art, the following will briefly introduce the drawings to be used in the embodiments. Obviously, the drawings in the following description are only some embodiments of the present application. For those of ordinary skill in the art, other drawings may be obtained according to these drawings without any creative labor.

DETAILED DESCRIPTION OF THE EMBODIMENTS

The technical solutions in the embodiments of the present application will be clearly and completely described below with reference to the drawings in the embodiments of the present application. Obviously, the described embodiments are only part of the embodiments of the present application, but not all of them. Based on the embodiment of the present application, all other embodiments obtained by ordinary technicians in the field without creative labor are within the scope of the present application.

In order to make the above objects, features and advantages of the present application more obvious and understandable, the present application will be explained in further detail below with reference to the drawings and detailed description.

Figure 2:
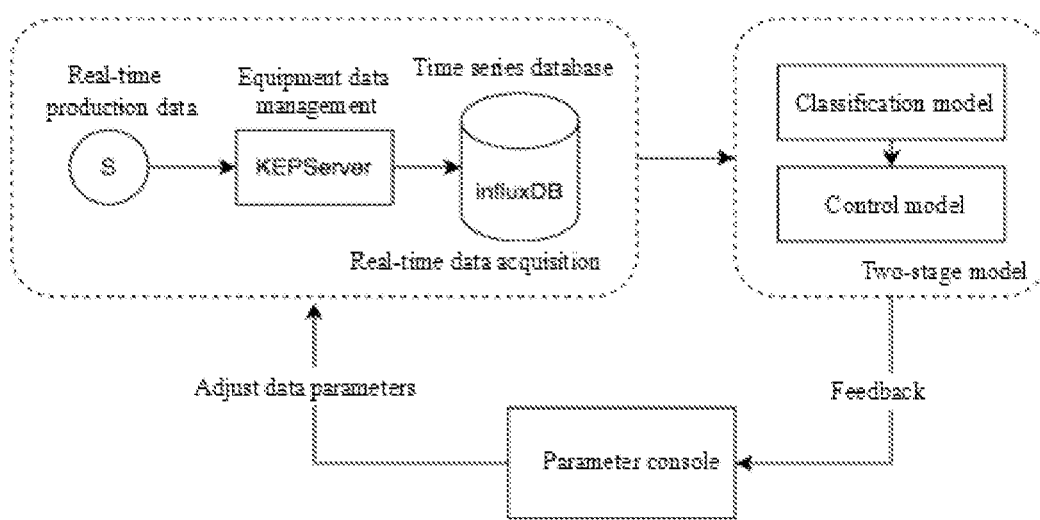
FIG. 2 is a system design diagram of an embodiment of the present application.

This embodiment provides an intelligent control system of the spunlace production line (as shown in FIG. 2), including:
a data acquiring module used for acquiring and storing real-time production line data; and the production line data includes cotton feeding roller values, real-time moisture values, real-time speed values and real-time gram weight values;
a data process module used for classifying and controlling the production line data, and giving adjustment opinions of cotton feeding roller parameters;
a parameter control module used for verifying parameter adjustment opinions and applying the parameter adjustment opinions to the intelligent control system; and
the data acquiring module, the data processing module and the parameter control module are connected in sequence.

The data acquiring module acquires the real-time production line data through sensors on the process production line, and saves the production line data into an influxDB time series database through KEPServer for subsequent modules to process and analyze.

The data acquiring module further includes a preprocessing unit; the preprocessing unit is used for cleaning, segmenting and extracting the production line data, performing a data enhancement processing by adopting an up-sampling method or a down-sampling method to obtain preprocessed data, and storing the preprocessed data into the influxDB time series database.

At present, the data obtained from spunlace production line include online detection data, spunlace data and carding machine data. The gram weight data will fluctuate up and down normally due to various factors. When the gram weight value exceeds the target value, the staff will keep the gram weight value within a stable range by adjusting the "cotton feeding roller" data in the carding machine data. The gram weight data and cotton feeding roller data are shown in Table 1 and Table 2 below.

TABLE 1

| Average gram weight | Target gram weight | Time |
|---|---|---|
| 35.2 | 35 | 2022 Feb. 27 23:10:00 |
| 35 | 35 | 2022 Feb. 27 23:10:00 |
| 35 | 35 | 2022 Feb. 27 23:10:00 |
| 36 | 35 | 2022 Feb. 27 23:10:00 |
| 36.6 | 35 | 2022 Feb. 27 23:10:00 |
| 36.7 | 35 | 2022 Feb. 27 23:10:00 |
| 36.2 | 35 | 2022 Feb. 27 23:10:00 |
| 34.7 | 35 | 2022 Feb. 27 23:10:00 |
| 34.9 | 35 | 2022 Feb. 27 23:10:00 |
| 35.3 | 35 | 2022 Feb. 27 23:10:00 |
| 35.2 | 35 | 2022 Feb. 27 23:10:00 |

TABLE 2

| Low-frame cotton feeding roller | Elevated cotton feeding roller | Time |
|---|---|---|
| 3.443 | 3.49417 | 2022 Feb. 27 23:10:00 |
| 3.47022 | 3.50506 | 2022 Feb. 27 23:10:00 |
| 3.43429 | 3.50506 | 2022 Feb. 27 23:10:00 |
| 3.46695 | 3.51051 | 2022 Feb. 27 23:10:00 |
| 3.46695 | 3.50289 | 2022 Feb. 27 23:10:00 |
| 3.45389 | 3.49744 | 2022 Feb. 27 23:10:00 |
| 3.46151 | 3.50833 | 2022 Feb. 27 23:10:00 |
| 3.46478 | 3.51051 | 2022 Feb. 27 23:10:00 |
| 3.45389 | 3.50289 | 2022 Feb. 27 23:10:00 |
| 3.42884 | 3.49417 | 2022 Feb. 27 23:10:00 |
| 3.46695 | 3.50833 | 2022 Feb. 27 23:10:00 |

Figure 3:
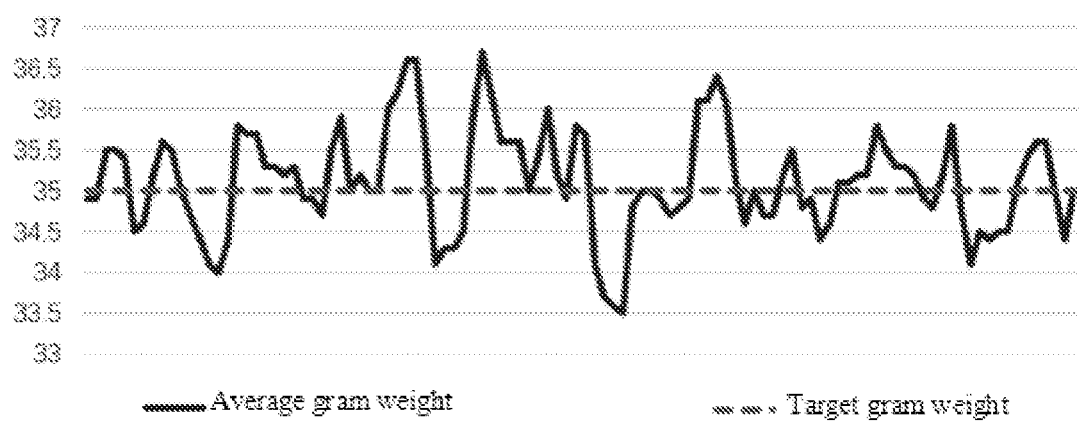
FIG. 3 is an example diagram of the normal trend of gram weight according to the embodiment of the present application.
Figure 4:
FIG. 4 is an example diagram of abnormal trend of gram weight according to the embodiment of the present application.

In order to show the trend of gram weight data changing with time more intuitively, FIG. 3 and FIG. 4 respectively select a time series of normal gram weight and a time series of abnormal gram weight to draw images. It can be seen that if the abnormal threshold is set at ±2, the gram weight curve of FIG. 3 always fluctuates randomly within the target gram weight range of 35±2, while the gram weight curve of FIG. 4 obviously keeps increasing in the second half, and it has exceeded the threshold value of 37 (that is, the target gram weight of 35+ threshold value of 2) many times. At this time, it is necessary to adjust the cotton feeding roller parameters to make the gram weight curve return to about 35. The target is to identify the abnormal trend as soon as possible during the real-time monitoring of the production line, and give the adjustment opinions of the cotton feeding roller.

As for the data of the spunlace production line, each batch of materials has different categories and different working conditions (for example, the adjustment times of workers are less and the gram weight is more unstable during handing-off), which will affect the final actual gram weight curve result. Meanwhile, due to the complicated situation on the production line, the on-off operation of the machine and the reading values of sensors in other abnormal situations are not directly marked in the acquired data, and the data obtained in these situations are often invalid abnormal values.

In order to use effective and reliable data when training the model, the acquired data is cleaned in the early stage. The main contents include: (1) performing data segmentation and extraction according to the stable working conditions provided by the production line; (2) performing data cleaning for some abnormal values which obviously deviate from the average value, or data with a very large jump in a period of time.

Figure 5:
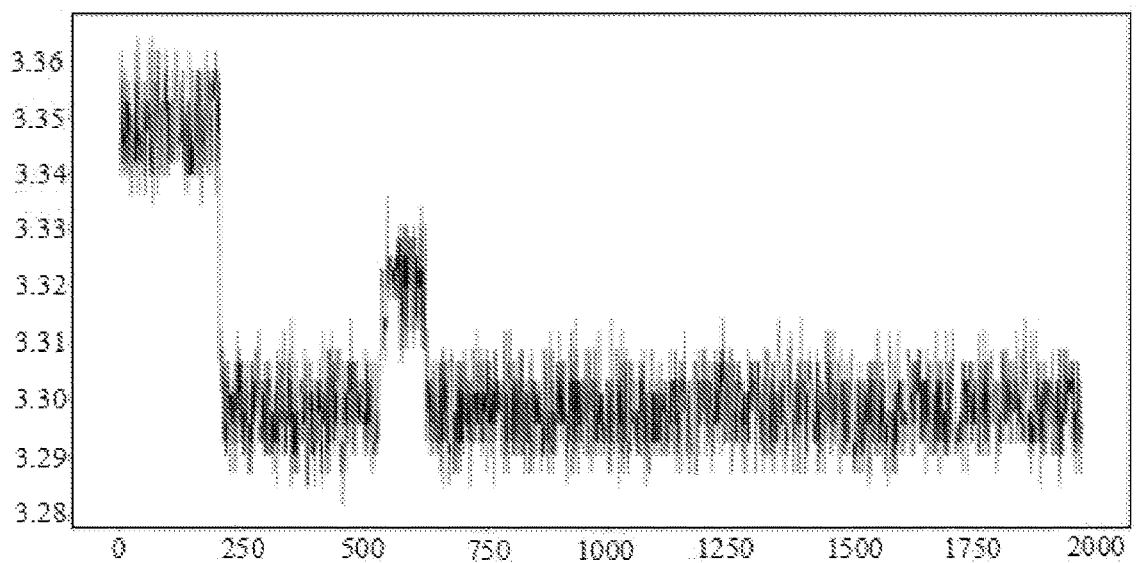
FIG. 5 is an example of cleaning of cotton feeding roller data according to the embodiment of the present application.
Figure 5:
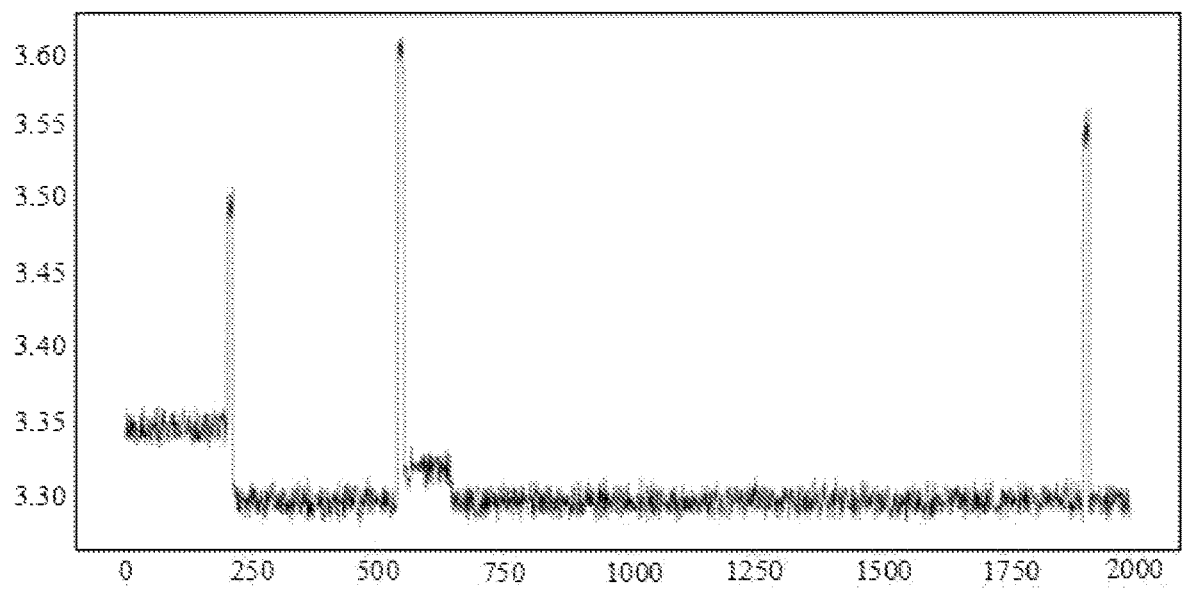

FIG. 5 shows an example of data cleaning for cotton feeding roller data. It can be seen that there are some meaningless jumps before cleaning. Skip the jumps during cleaning, and smooth the average.

The abnormal data samples on the actual production line account for a small proportion, and most of the data still fluctuate within the normal range, so there is a problem of data imbalance, which will lead to the trained model biased towards the majority of results. Meanwhile, the lack of abnormal samples may also affect the characteristics of abnormal trends in model learning. Therefore, some data enhancement methods are adopted in this embodiment to solve this problem.

Figure 6:
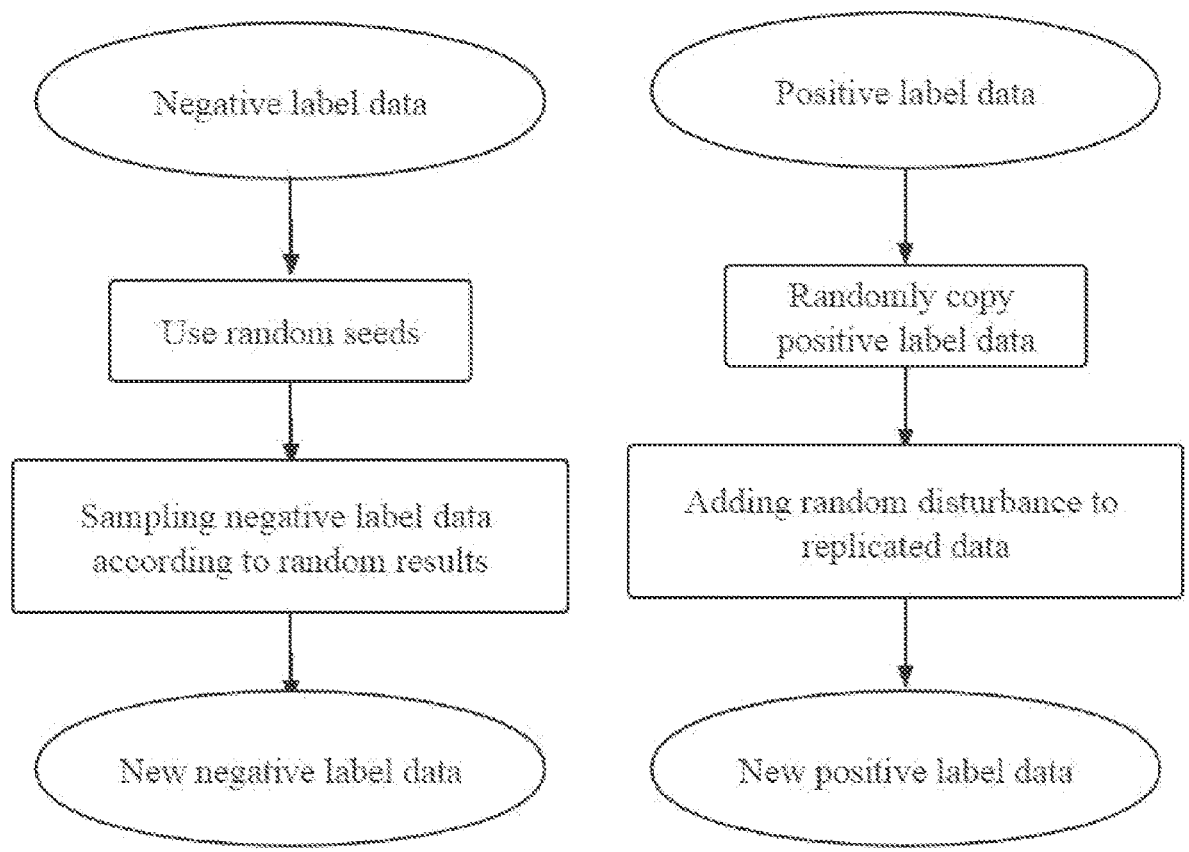
FIG. 6 is a brief flow chart of down-sampling and up-sampling methods according to an embodiment of the present application.

Specifically, in the process of training, the method of down-sampling or up-sampling is used to solve the problem of data imbalance, so that the data volume of different labels can reach a basically balanced state, which is convenient for the subsequent actual model analysis. FIG. 6 shows a brief flow chart of down-sampling and up-sampling methods.

The data processing module includes:
a classifying unit used for predicting the probability of exceeding the gram weight threshold in the future through the classifying model;
a control unit used to set up automatic control closed loop and give the adjustment opinions of cotton feeding roller parameters.

Figure 7:
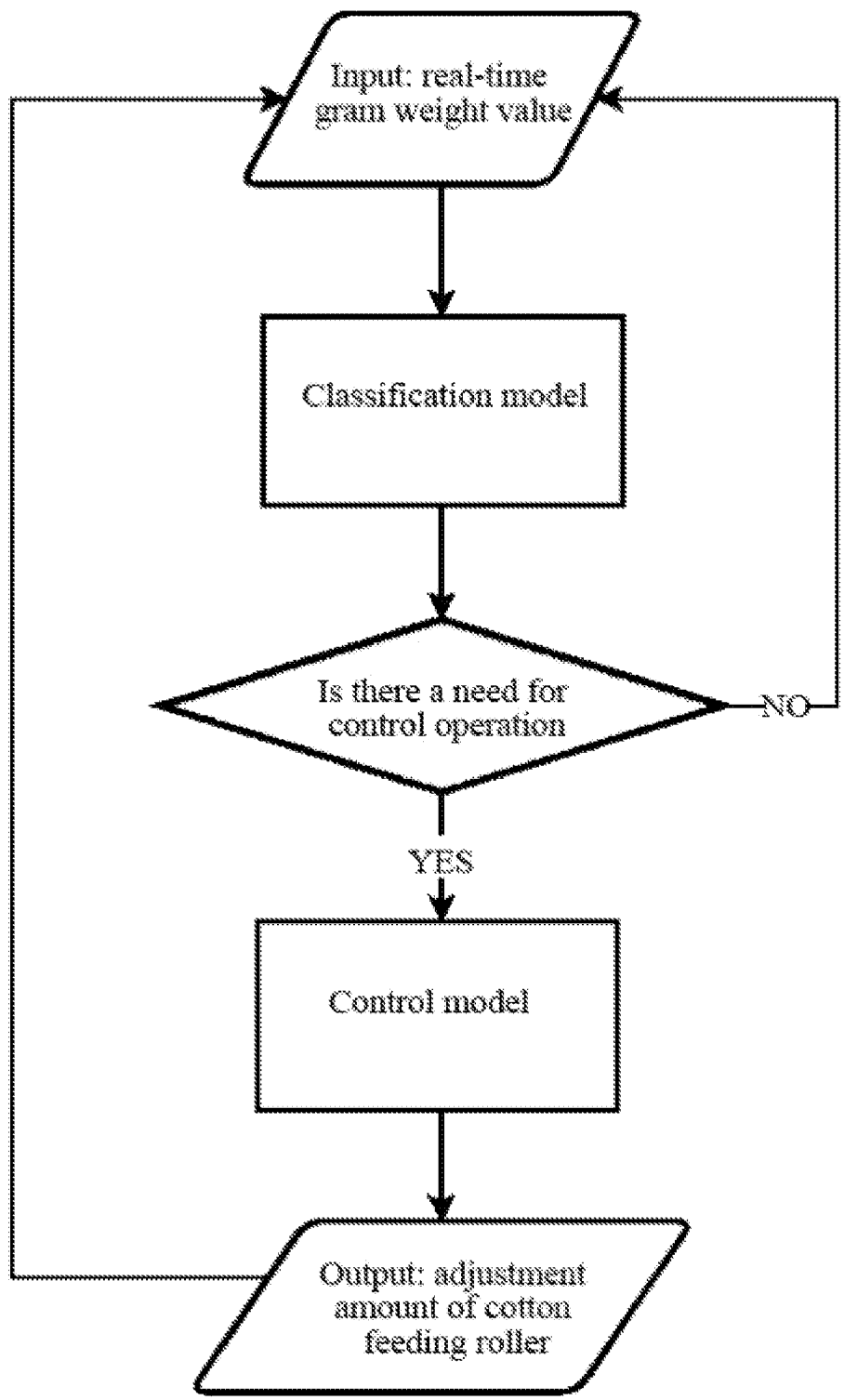
FIG. 7 is a model design diagram of an embodiment of the present application.

In order to predict the weight trend and give corresponding adjustment suggestions, a two-stage model is proposed to complete these tasks, including a classifying model and a control model. The specific model design diagram is shown in FIG. 7. The classifying model defines a multi-classification problem, aiming at predicting the possibility of exceeding the gram weight threshold in the future according to the current real-time window data. Firstly, the model uses the historical data of Yongxin process production line for training, and through the historical data, the characteristic data related to gram weight and cotton feeding roller are extracted, and a time series classifying model is built for prediction. The control model uses the historical manual adjustment of cotton feeding roller and the corresponding historical data of gram weight change to build a model, build an automatic control closed loop, and give the adjustment opinions of cotton feeding roller parameters.

The classifying model is used for classifying according to real-time production line data, obtaining the current data state and classification result, defining the label type of the classification result, and judging whether the adjustment operation is needed according to the classification result; if the adjustment operation is needed, the classification result is input into the control unit for further processing; if the adjustment operation is not needed, new data is continuously input.

The goal of the classifying model is to classify the status of the current data according to the real-time data, and then make the decision whether to adjust the operation according to the classification results.

Because the obtained data has not been manually marked, it is necessary to mark the data through certain judgment standards. According to the existing experience of spunlace production line, the following empirical rules are summarized for consideration:
(1) small amplitude fluctuations can be ignored, and medium and small amplitude fluctuation in gram weight can also be ignored;
(2) medium and small amplitude fluctuation with order of minutes continuously higher than the target value needs attention, and two or three consecutive volumes small amplitude fluctuation slightly higher than the target value need attention;
(3) for cost reasons, staying above the target value requires more attention than staying below the target value.

According to these rules, the judgment of whether or not to make adjustment depends largely on whether there are cases that are higher than the target value in a certain period of time, and whether there are cases that are higher than the target value in a small period of time. According to the above experience and actual production situation, in this embodiment, the threshold of abnormal samples exceeding the target value is set to ±2, and the label is defined as shown in Table 3 (the label definition is only an example, and will be changed according to the actual production situation).

TABLE 3

| Label | Meaning | Judgement standard |
|---|---|---|
| VL | Strong upper supersample | Whether the average value of the sample is greater than (target value +2) in the next 20 time points |
| L | Upper supersample | Whether the average value of the samplei s greater than (target value +1) in the next 20 time points |
| N | Normal sample | Whether the sample will always fluctuate within the target range in the next 20 time points |
| S | Lower supersample | Whether the average value of the sample is less than (target value −1) in the next 20 time points |
| VS | Strong lower supersample | Whether the average value of the sample is less than (target value −2) in the next 20 time points |

Figure 8:
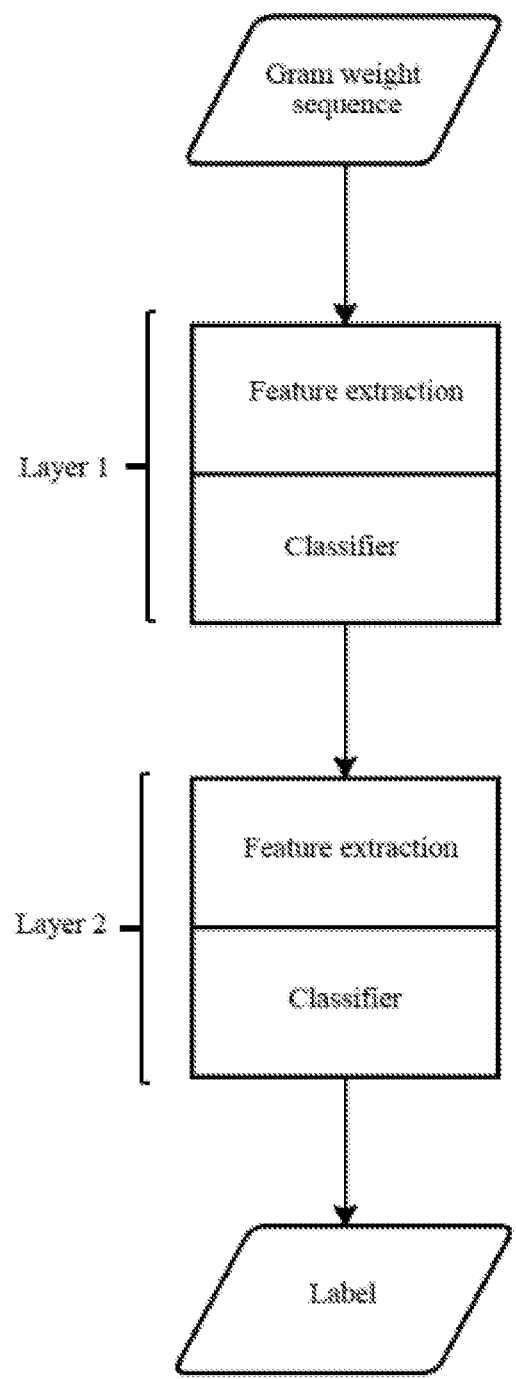
FIG. 8 is a schematic diagram of the classifying model design of the embodiment of the present application.

Because it is hoped that the label can predict the change of the future gram weight trend through the historical window value, the classifying model design as shown in FIG. 8 is adopted. The production line itself has a high demand for model sensitivity, and the abnormal trend needs to be adjusted as soon as possible. Therefore, the accuracy of classification may be well improved by adopting a double-layer classifier.

The first classifier adopts a random forest model. Random forest is an algorithm that integrates multiple trees through the idea of integrated learning. Its basic unit is decision trees, and each decision tree is a classifier. For an input sample, N trees will have N classification results. The random forest integrates all the classified voting results, and designates the category with the most voting times as the final output. Random forests can effectively train on large data sets, and have the advantages of fast training speed and high accuracy.

Specifically, in the feature extraction stage, the features of the historical gram weight window and the cotton feeding roller historical window are extracted and input into the model. Finally, the predicted percentage of each label is output by the random forest algorithm.

Figure 9:
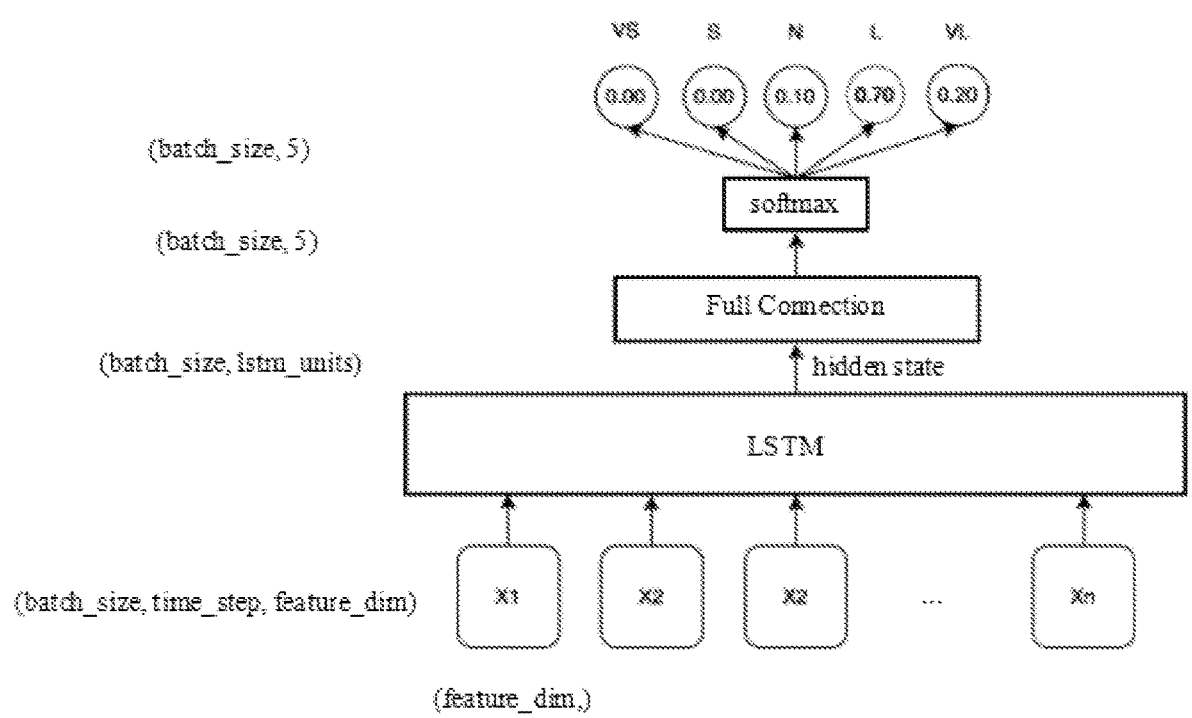
FIG. 9 is a schematic diagram of LSTM model of an embodiment of the present application.

The second classifier adopts the recurrent neural network model LSTM shown in FIG. 9. The input is the output label confidence history window of classifier 1, and the output is the defined label.

LSTM adopts cross entropy loss function, historical data is trained by a small batch gradient descent, and real-time data is fine-tuned by a random gradient descent. The hidden state output in the last time step aggregates the information of all time steps, and hidden state is input to the full connection layer activated by softmax to get the probability of each set label.

LSTM can effectively aggregate information of multiple time steps, and automatically extract important features by using the feature screening function of deep network. LSTM uses a forget gate and an output gate to control the circulation and loss of features in each time step, which can effectively deal with the problem of long-term dependence in long time steps, and make the model learn the influence of early time steps on future time points.

The control unit includes:
a prediction model used to predict the cotton feeding roller value output by the system in the future according to the historical production line data and the predicted percentage of labels;
an optimization sub-unit used for adjusting the cotton feeding roller value through the prediction model between a variable quantity of gram weight and the variable quantity of cotton feeding roller, using the prediction percentage of labels output by the classifying model as a membership degree of the classification of the production state, and outputting an optimal adjustment amount of cotton feeding roller based on a model conversion.

After inputting the real-time data, the adjustment opinions will be output for the on-site operators to verify. The final adjustment opinions will be directly applied to the control system of the process line, and the console will change the specific parameters of the process line in real time according to the adjustment opinions.

The goal of the control model is to predict the future change state of the gram weight based on the current prediction, and to adjust and feedback the parameters of the cotton feeding roller. Here the related concepts of automatic control theory are introduced to help adjust the feedback.

Figure 10:
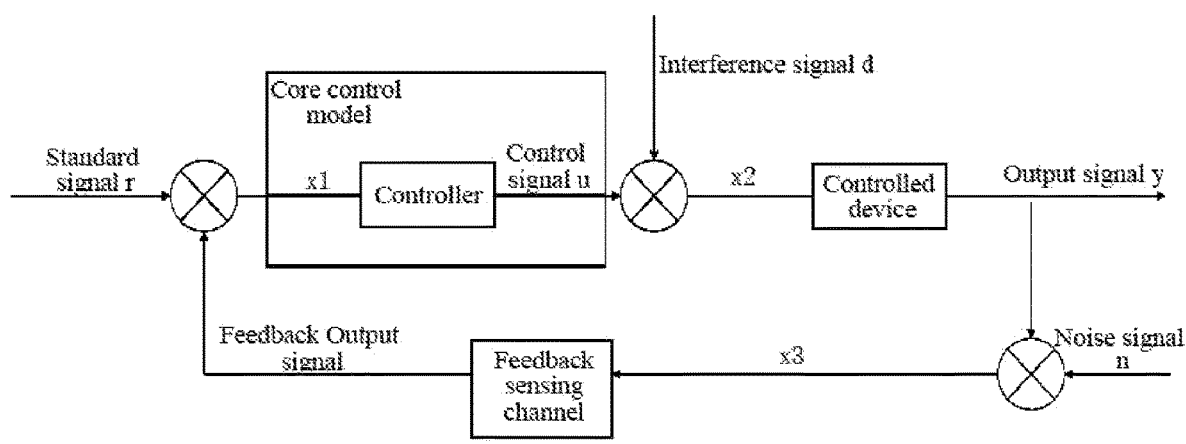
FIG. 10 is a structural diagram of a conventional control system according to an embodiment of the present application.

In the field of industrial process control, for a long time, industrial controllers mainly adopt the control method based on feedback regulation. By feeding back the system response measured by sensors to the input of the controller, the function of tracking the set value of the system response is realized. FIG. 10 shows the conventional control system structure. PID control is such a control method based on feedback regulation. Although the conventional control scheme represented by PID can realize non-differential regulation, it is difficult to guarantee the rapid control and the timely response in the control of complex working conditions such as large delay and inertia.

Referring to the basic ideas of model predictive control and fuzzy control, the control model proposed in this embodiment uses the following steps to control.

Prediction model: the prediction model is the basis of model prediction control. The main function is to predict the future output of the system according to the historical information and future input of the object. Since the future output state has been predicted by the classifying model in the preceding step of the control model, the classifying model may be reused as the result of our prediction model. The prediction model also saves the running time of the model in online detection.

Figure 11:
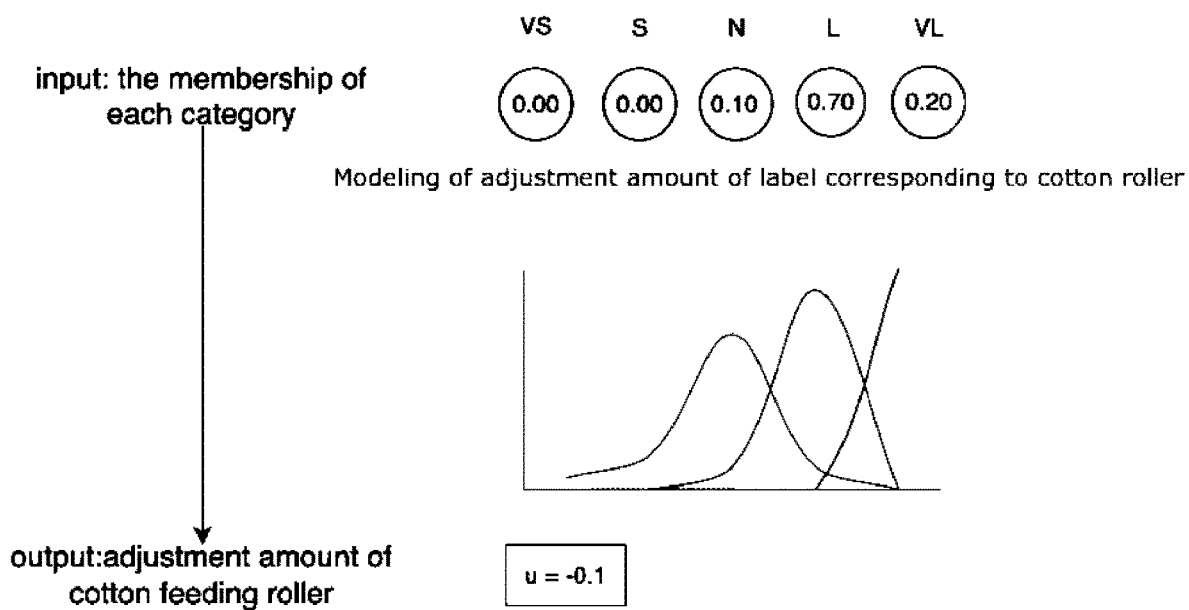
FIG. 11 is a schematic diagram of optimal control according to an embodiment of the present application.

Optimization control: the model predictive control determines the control function through the optimization of a certain performance indicator. In off-line training, the mathematical model between the change of gram weight and the change of cotton feeding roller will be established through the historical data of gram weight and cotton feeding roller, and the mathematical model is used as the basis for adjusting the value of the cotton feeding roller. Then, the label prediction possibility output by the classifying model is used as the membership degree of each classification, and the optimal adjustment amount of the cotton feeding roller is found through model conversion as the output of this optimization step. FIG. 11 is a schematic diagram of optimal control.

The parameter control module includes a feedback correction unit. In order to prevent the control from deviating from the ideal state due to model mismatch or environmental interference, the feedback correction unit will make a new prediction at each new sampling moment, and use this real-time information to correct the prediction result based on the model, and then make a new optimization.

Figure 12:
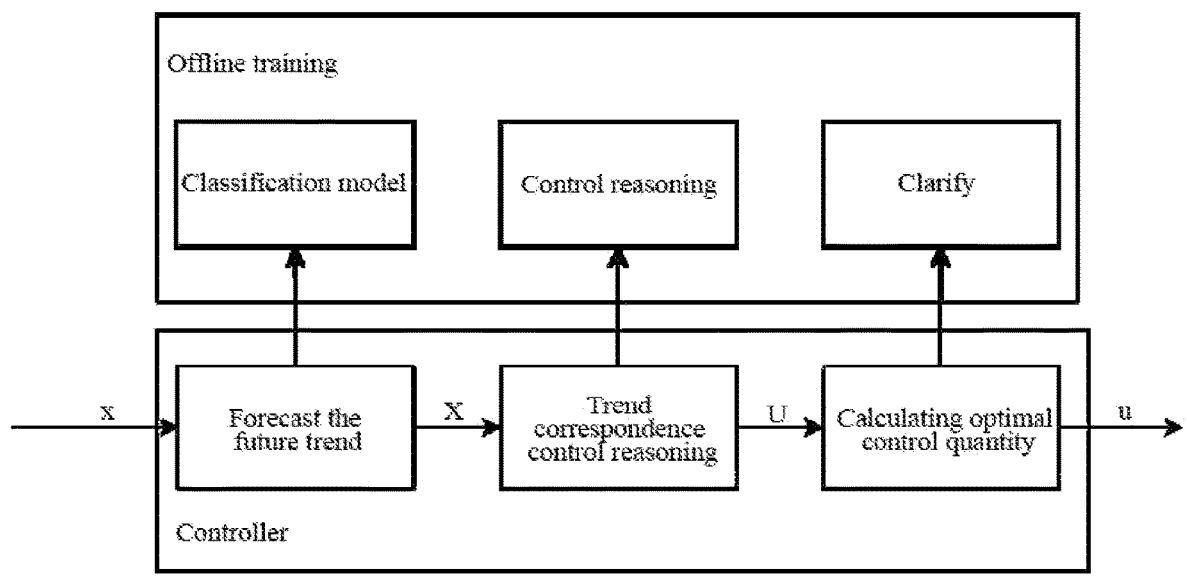
FIG. 12 is a structural diagram of a control model of an embodiment of the present application.

The overall structure of the control model is shown in FIG. 12. The relations between the change of gram weight and the change of cotton feeding roller parameters can be better established, the opinions of parameter adjustment can be output to workers in an intelligent way, and the automatic adjustment can be completed, which saves a lot of manual work on the basis of ensuring accurate adjustment.

Figure 1:
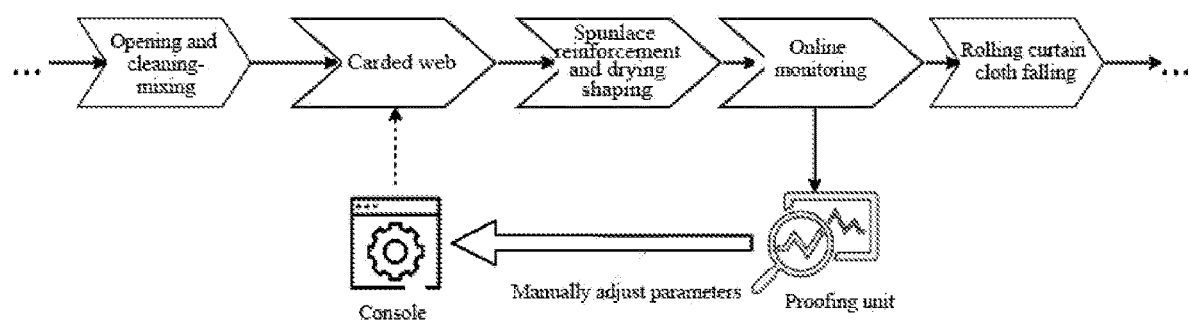
FIG. 1 is a flow diagram of the prior art in the present application.
Figure 13:
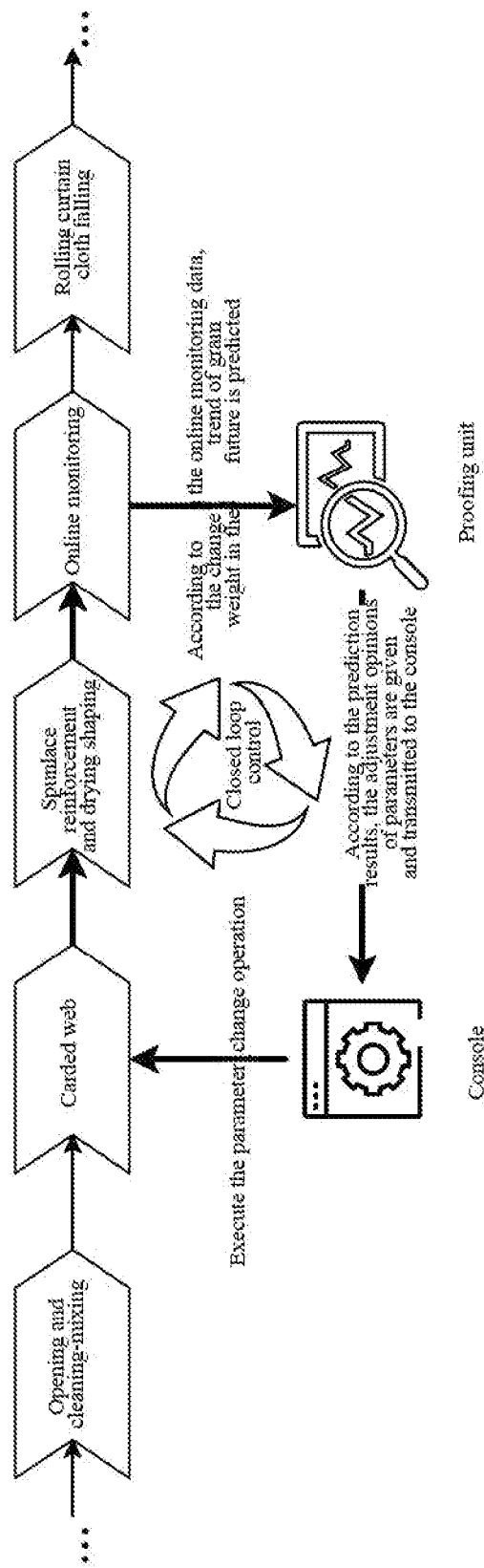
FIG. 13 is a design flow chart of an embodiment of the present application.

FIG. 13 shows the process flow of applying the intelligent control system, including using the classifying model to predict the change trend in the future, and using the feedback model to predict the parameter change. This process optimizes the original manual intervention parameter adjustment process in FIG. 1, and completes an automatic closed loop of "monitoring-adjusting-changing" through intelligent control.

The above-mentioned embodiments only describe the preferred mode of the application, but do not limit the scope of the application. On the premise of not departing from the design spirit of the application, all kinds of modifications and improvements made by ordinary technicians in the field to the technical scheme of the application shall fall within the scope of protection determined by the claims of the application.

What is claimed is:

1. An intelligent control system of a spunlace production line implemented in a computer system using a set of computer-executable instructions, comprising:
   a data acquiring module used for acquiring and storing real-time production line data; wherein the real-time production line data comprises cotton feeding roller values, real-time moisture values, real-time speed values and real-time gram weight values;
   a data process module used for classifying and controlling the real-time production line data, and giving adjustment opinions of cotton feeding roller parameters; and
   a parameter control module used for verifying parameter adjustment opinions and applying the parameter adjustment opinions to the intelligent control system,
   wherein the data acquiring module, the data processing module and the parameter control module are connected in sequence;
   wherein the data processing module comprises:
   a classifying unit used for predicting a probability of exceeding a gram weight threshold in future through a classifying model;
   a control unit used for setting up an automatic control closed loop and giving the adjustment opinions of cotton feeding roller parameters; the classifying model is used for classifying according to the real-time production line data to obtain current production states and classification results; defining label types for the classification results, and judging whether an adjustment operation is needed or not according to the classification results; wherein if the adjustment operation is needed, the classification results are input into the control unit for a further processing, and if the adjustment operation is not needed, new data is continuously re-input.

2. The intelligent control system of a spunlace production line according to claim 1, wherein the data acquiring module acquires the real-time production line data through sensors on the process production line, and saves the real-time production line data into a time series database through a data integration software program for subsequent modules to process and analyze.

3. The intelligent control system of a spunlace production line according to claim 2, wherein the data acquiring module further comprises a preprocessing unit; the preprocessing unit is used for cleaning, segmenting and extracting the real-time production line data, performing a data enhancement processing by adopting an up-sampling method or a down-sampling method to obtain preprocessed data, and storing the preprocessed data into the time series database.

4. The intelligent control system of a spunlace production line according to claim 1, wherein the classifying model adopts a double-layer classifier; the double-layer classifier comprises a first classifier and a second classifier; and an output quantity of the first classifier is taken as an input quantity of the second classifier.

5. The intelligent control system of a spunlace production line according to claim 4, wherein the first classifier adopts a random forest model, extracts features of a historical gram weight window and a historical cotton feeding roller window, inputs the features into the random forest model, and outputs a predicted percentage of each label; the second classifier inputs a historical window of the predicted percentage of the output label of the first classifier by adopting a long short-term memory (LSTM) model, and outputs a predicted label of a production state; the LSTM model uses a small batch gradient descent method to train historical data, adjusts real-time data through random gradient descent, and obtains a probability of the label of the production state through a full connection layer activated by softmax.

6. The intelligent control system of a spunlace production line according to claim 5, wherein the control unit comprises:
   a prediction model used to predict the cotton feeding roller value output by the system in future according to the historical production line data and the predicted percentage of labels;
   an optimization sub-unit used for adjusting the cotton feeding roller value through the prediction model between a variable quantity of gram weight and a variable quantity of cotton feeding roller, using the prediction percentage of the labels output by the classifying model as a membership degree of the classification of the production state, and outputting an optimal adjustment amount of the cotton feeding roller based on a model conversion.

7. The intelligent control system of a spunlace production line according to claim 1, wherein the parameter control module comprises a feedback correction unit; and the feedback correction unit is used for re-predicting at each new sampling moment, and correcting a prediction result using real-time information, and then performing a new optimization.

\* \* \* \* \*